(12) United States Patent
Melsheimer et al.

(10) Patent No.: US 9,248,253 B2
(45) Date of Patent: Feb. 2, 2016

(54) WINGED CATHETER ASSEMBLY

(75) Inventors: Jeffry S. Melsheimer, Springville, IN (US); Christopher D. Bosel, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 2327 days.

(21) Appl. No.: 11/842,338

(22) Filed: Aug. 21, 2007

(65) Prior Publication Data

US 2009/0054825 A1    Feb. 26, 2009

(51) Int. Cl.
*A61M 25/14* (2006.01)
*A61M 1/14* (2006.01)
*A61M 25/00* (2006.01)

(52) U.S. Cl.
CPC .......... *A61M 25/003* (2013.01); *A61M 25/007* (2013.01); *A61M 25/0075* (2013.01); *A61M 2025/0031* (2013.01); *A61M 2025/0037* (2013.01)

(58) Field of Classification Search
USPC ............... 604/4.01, 6.05, 6.1, 9, 30, 35, 6.16, 604/99.04, 264, 268
See application file for complete search history.

(56) References Cited

U.S. PATENT DOCUMENTS

| | | | |
|---|---|---|---|
| 3,938,530 A | 2/1976 | Santomieri | 128/349 R |
| 3,946,741 A | 3/1976 | Adair | 128/347 |
| 4,129,129 A | 12/1978 | Amrine | 128/214 R |
| 4,134,402 A | 1/1979 | Mahurkar | 128/214 R |
| 4,154,242 A | 5/1979 | Termanini | 128/349 R |
| 4,431,426 A * | 2/1984 | Groshong et al. | 604/523 |
| 4,493,696 A | 1/1985 | Uldall | 604/43 |
| RE31,855 E | 3/1985 | Osborne | 604/161 |
| 4,581,025 A | 4/1986 | Timmermans | 604/264 |
| 4,583,968 A * | 4/1986 | Mahurkar | 604/43 |
| 4,643,711 A | 2/1987 | Bates | 604/4 |
| 4,655,745 A | 4/1987 | Corbett | 604/49 |
| 4,680,029 A | 7/1987 | Ranford et al. | 604/280 |
| 4,692,141 A | 9/1987 | Mahurkar | 604/43 |
| 4,733,669 A | 3/1988 | Segal | 128/663 |
| 4,772,268 A | 9/1988 | Bates | 604/174 |
| 4,808,163 A | 2/1989 | Laub | 604/105 |
| 4,878,893 A | 11/1989 | Chin | 604/21 |
| 4,904,238 A | 2/1990 | Williams | 604/43 |
| 4,936,826 A * | 6/1990 | Amarasinghe | 604/507 |
| 4,973,301 A | 11/1990 | Nissenkorn | 604/8 |
| 4,995,865 A * | 2/1991 | Gahara et al. | 604/43 |
| 4,995,868 A | 2/1991 | Brazier | 604/105 |

(Continued)

FOREIGN PATENT DOCUMENTS

| | | | |
|---|---|---|---|
| EP | 0 301 854 A2 | 2/1989 | ............ A61M 25/00 |
| WO | WO 01/19425 A1 | 3/2001 | ............. A61L 29/06 |

(Continued)

*Primary Examiner* — Adam Marcetich
(74) *Attorney, Agent, or Firm* — Brinks Gilson & Lione

(57) ABSTRACT

A catheter assembly for use in extracorporeal treatment of a body fluid comprises a catheter body having a plurality of lumens extending therein. The catheter body has an aspiration port in communication with a first lumen for transporting fluid withdrawn from a body vessel to a treatment instrument, such as a dialyzer, and an infusion port in communication with a second lumen for return of treated fluid to the vessel. The catheter body includes a wing-like flap portion extending radially from the catheter body and defining the aspiration port. The flap portion is configured and arranged to space the aspiration port from a wall of the body vessel.

15 Claims, 5 Drawing Sheets

(56) References Cited

U.S. PATENT DOCUMENTS

| | | | |
|---|---|---|---|
| 5,030,201 A * | 7/1991 | Palestrant | 604/22 |
| 5,106,368 A | 4/1992 | Uldall et al. | 604/43 |
| 5,156,597 A | 10/1992 | Verreet et al. | 604/175 |
| 5,193,533 A | 3/1993 | Body et al. | 128/207.14 |
| 5,221,256 A | 6/1993 | Mahurkar | 604/43 |
| 5,250,034 A * | 10/1993 | Appling et al. | 604/164.02 |
| 5,275,610 A | 1/1994 | Eberbach | 606/198 |
| 5,352,198 A | 10/1994 | Goldenberg et al. | 604/95 |
| 5,360,397 A * | 11/1994 | Pinchuk | 604/27 |
| 5,409,460 A | 4/1995 | Krumme | 604/107 |
| 5,443,449 A | 8/1995 | Buelna | 604/105 |
| 5,486,159 A | 1/1996 | Mahurkar | 604/4 |
| 5,509,897 A | 4/1996 | Twardowski et al. | 604/43 |
| 5,509,900 A | 4/1996 | Kirkman | 604/104 |
| 5,514,112 A | 5/1996 | Chu et al. | 604/267 |
| 5,518,498 A | 5/1996 | Lindenberg et al. | 600/30 |
| 5,522,400 A | 6/1996 | Williams | 128/772 |
| 5,571,093 A | 11/1996 | Cruz et al. | 604/270 |
| 5,681,280 A | 10/1997 | Rusk et al. | 604/95 |
| 5,702,365 A * | 12/1997 | King | 604/105 |
| 5,713,853 A | 2/1998 | Clark et al. | 604/53 |
| 5,749,826 A | 5/1998 | Faulkner | 600/29 |
| 5,817,067 A | 10/1998 | Tsukada | 604/256 |
| 5,857,464 A | 1/1999 | Desai | 128/658 |
| 5,885,258 A | 3/1999 | Sachdeva et al. | 604/281 |
| 5,888,196 A | 3/1999 | Bonutti | 600/204 |
| 5,957,900 A | 9/1999 | Ouchi | 604/264 |
| 6,001,079 A | 12/1999 | Pourchez | 604/43 |
| 6,033,397 A | 3/2000 | Laufer et al. | 606/27 |
| 6,052,612 A * | 4/2000 | Desai | 600/435 |
| 6,071,263 A | 6/2000 | Kirkman | 604/104 |
| 6,177,049 B1 | 1/2001 | Schnell et al. | 422/44 |
| 6,238,412 B1 | 5/2001 | Dubrul et al. | 606/200 |
| 6,270,490 B1 | 8/2001 | Hahnen | 604/509 |
| 6,283,940 B1 | 9/2001 | Mulholland | 604/96.01 |
| 6,293,958 B1 * | 9/2001 | Berry et al. | 606/191 |
| 6,336,933 B1 * | 1/2002 | Parodi | 606/139 |
| 6,409,700 B1 | 6/2002 | Siegel, Jr. et al. | 604/43 |
| 6,454,775 B1 | 9/2002 | Demarais et al. | 606/128 |
| 6,461,321 B1 | 10/2002 | Quinn | 604/43 |
| 6,475,207 B1 | 11/2002 | Maginot et al. | 604/508 |
| 6,517,529 B1 | 2/2003 | Quinn | 604/528 |
| 6,527,737 B2 | 3/2003 | Kaneshige | 604/48 |
| 6,547,761 B2 | 4/2003 | Liu | 604/104 |
| 6,558,349 B1 | 5/2003 | Kirkman | 604/104 |
| 6,558,350 B1 | 5/2003 | Hart et al. | 604/104 |
| 6,569,150 B2 | 5/2003 | Teague et al. | 604/524 |
| 6,579,261 B1 * | 6/2003 | Kawamura | 604/105 |
| 6,579,302 B2 | 6/2003 | Duerig et al. | 606/198 |
| 6,701,180 B1 * | 3/2004 | Desai | 600/435 |
| 6,767,339 B2 * | 7/2004 | Reydel | 604/175 |
| 6,939,327 B2 * | 9/2005 | Hall et al. | 604/164.05 |
| 2001/0011182 A1 | 8/2001 | Dubrul et al. | 606/200 |
| 2001/0018576 A1 | 8/2001 | Quinn | 604/264 |
| 2002/0072768 A1 | 6/2002 | Ginn | 606/213 |
| 2002/0143292 A1 | 10/2002 | Flinchbaugh | 604/107 |
| 2002/0177822 A1 | 11/2002 | St. Cyr et al. | 604/264 |
| 2003/0032918 A1 | 2/2003 | Quinn | 604/43 |
| 2003/0139763 A1 | 7/2003 | Duerig et al. | 606/198 |
| 2005/0148929 A1 | 7/2005 | Gingles | 604/95.04 |
| 2005/0261663 A1 * | 11/2005 | Patterson et al. | 604/508 |
| 2006/0253063 A1 * | 11/2006 | Schweikert | 604/30 |

FOREIGN PATENT DOCUMENTS

| | | | | |
|---|---|---|---|---|
| WO | WO 02/064202 A3 | 8/2002 | | A61M 25/00 |
| WO | WO 2005/049125 A1 | 6/2005 | | A61M 25/04 |

* cited by examiner

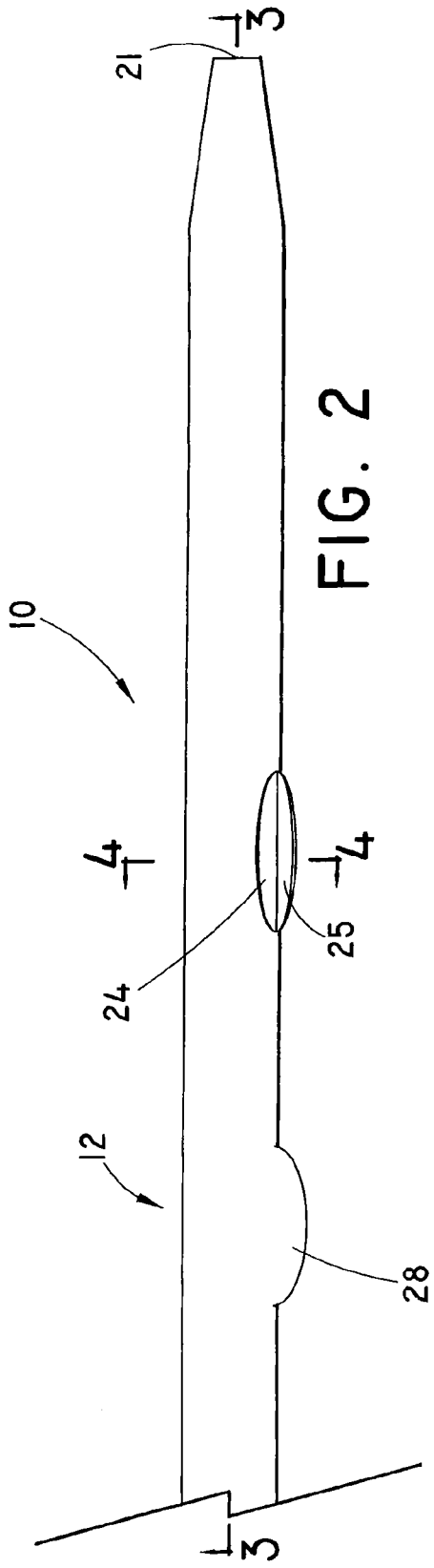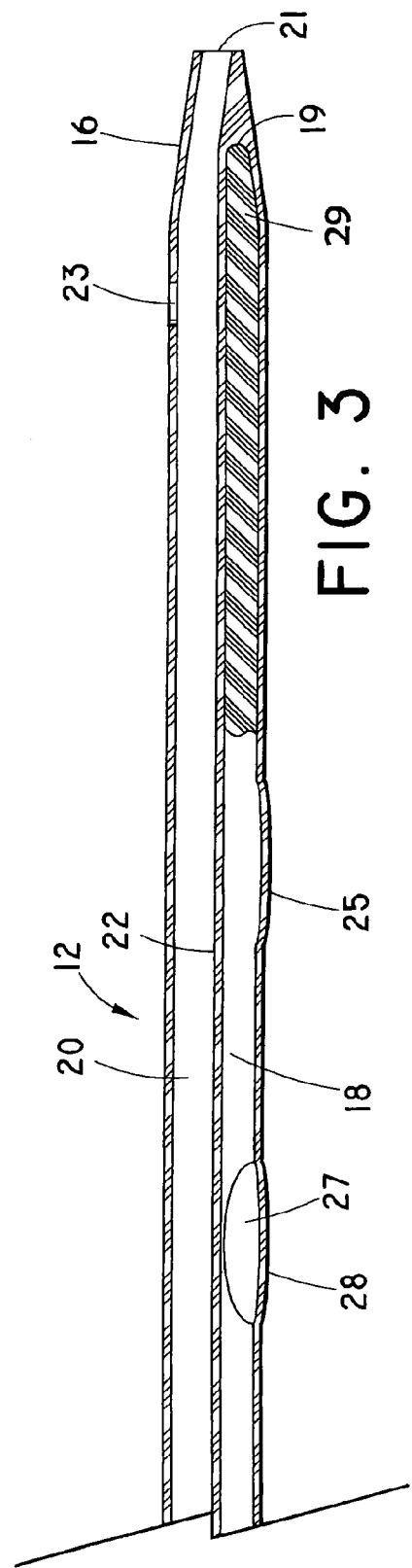

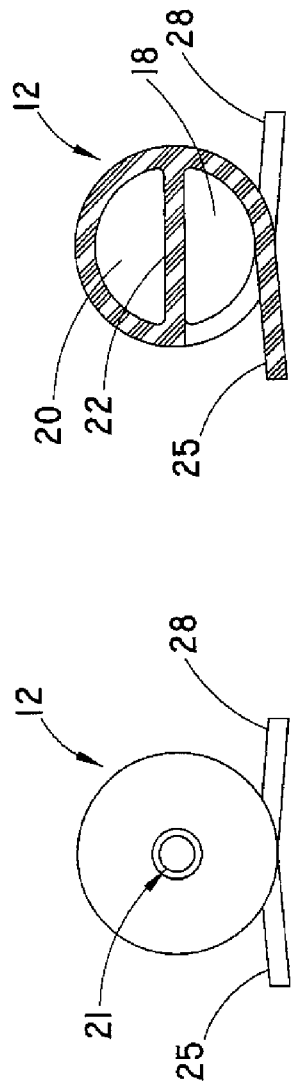
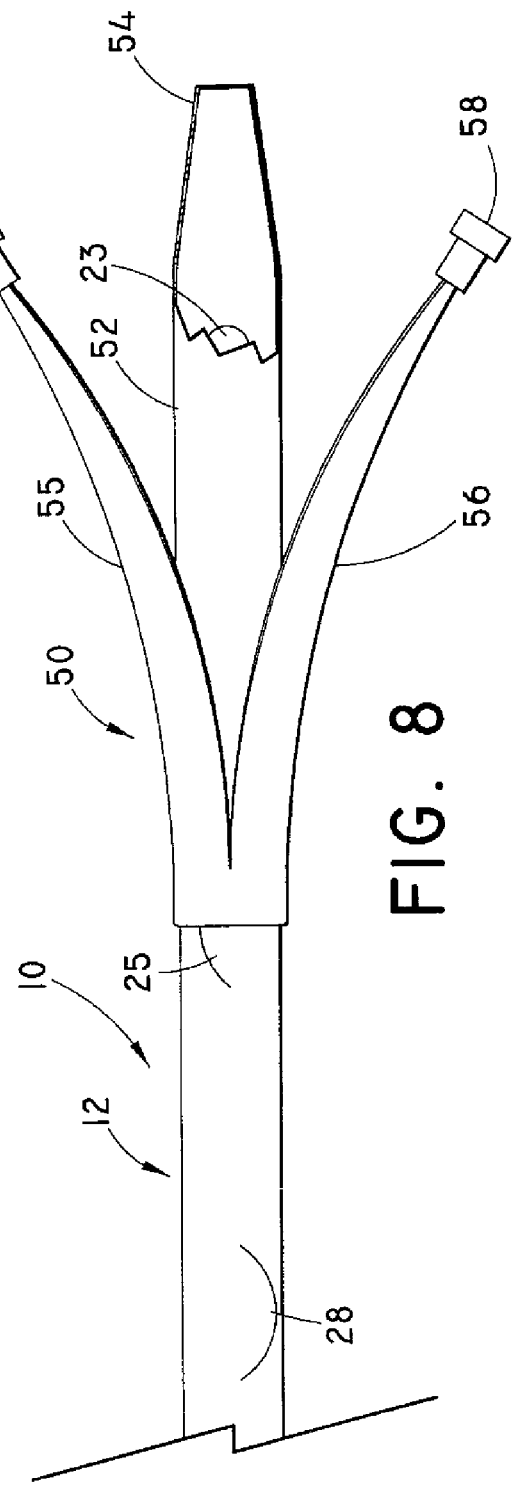

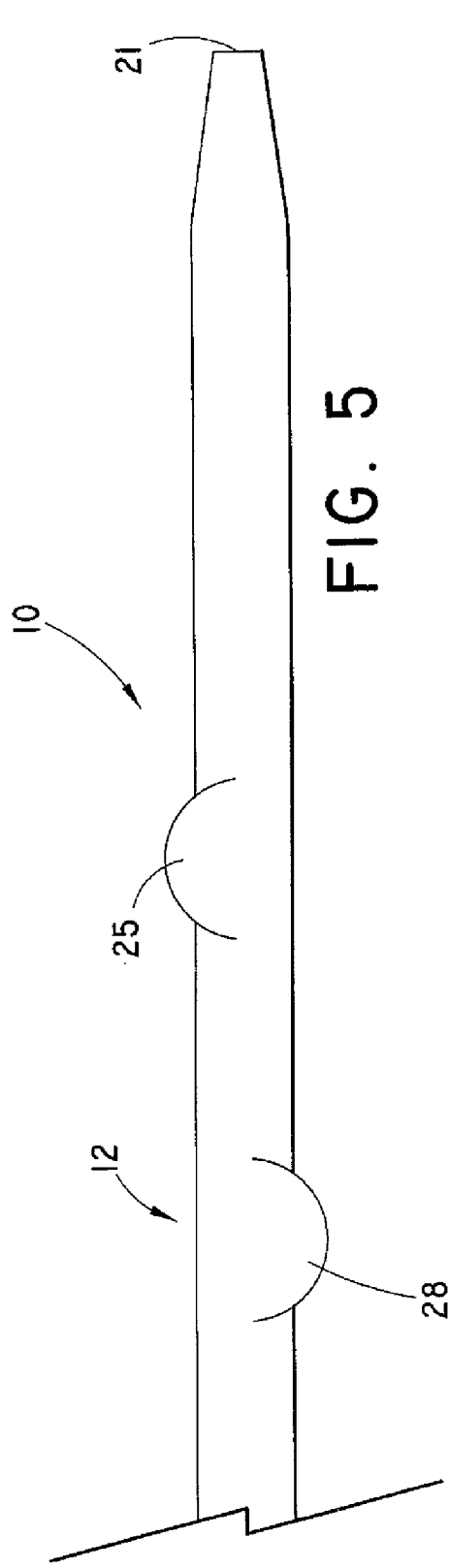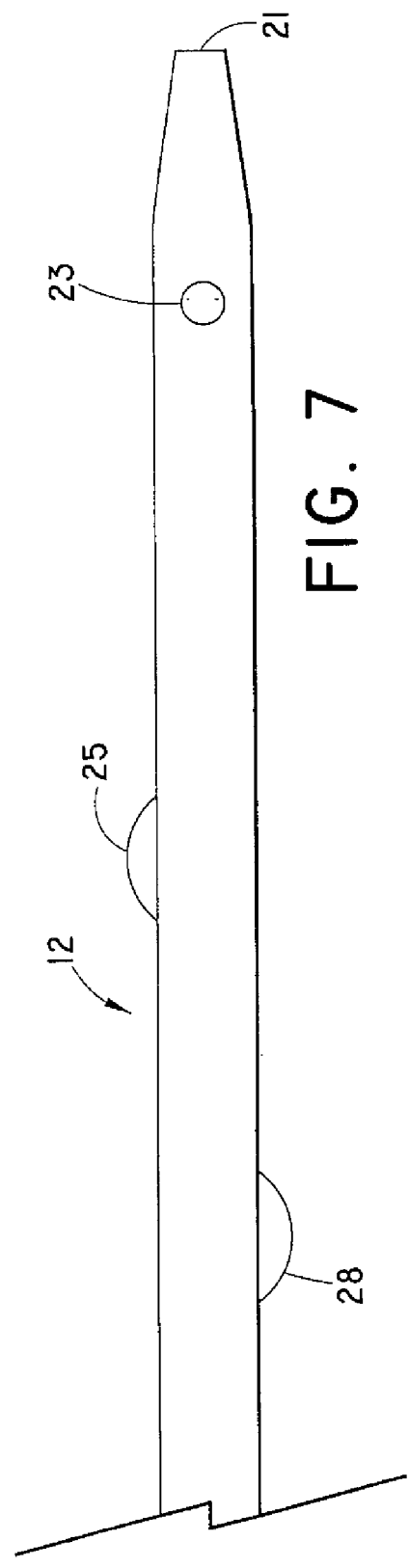

WINGED CATHETER ASSEMBLY

BACKGROUND

1. Technical Field

The present application relates generally to a catheter for use in transporting fluids, and more particularly, to a multi-lumen catheter assembly for transporting fluids from the patient's body for extracorporeal treatment, and returning the treated fluids to the body.

Multi-lumen catheters are commonly used for transporting bodily fluids during an extracorporeal treatment process for the bodily fluid. A fluid is withdrawn from the body through one of the lumens, generally referred to as the aspiration, or withdrawal, lumen. The fluid is subjected to a treatment process, and thereafter returned to the body through the other lumen, generally referred to as the infusion, or return, lumen.

In many cases, the extracorporeal treatment involves a hemodialysis procedure. During hemodialysis, blood is withdrawn from a blood vessel through the aspiration lumen and routed to a dialyzer for treatment. The cleansed blood is then returned to the vessel through the infusion lumen. When such a catheter is used for hemodialysis, whether for acute (short-term, generally thirty days or less), or longer term hemodialysis, it is generally inserted into the body through either the internal jugular vein, subclavian vein or femoral vein. In addition to hemodialysis, extracorporeal catheters can also be used for other procedures, such as pheresis and hemofiltration, in which a fluid is removed from the body for treatment and later returned to the body.

A variety of hemodialysis catheters are commercially available. Among the types of commercially available catheters are: 1) a dual lumen catheter wherein one lumen (e.g., the blood infusion lumen) terminates distal to the other lumen (e.g., the blood aspiration lumen). Some catheters of this type are provided with a midline split (e.g., the Uldall catheter), while others do not have such a split (e.g., the COOK® DDS catheter); 2) catheters having a slitted valve in the distal tip that acts as a pressure valve opening. This valve opens inwardly for blood aspiration, outwardly for blood infusion, and remains closed when not in use (e.g., the Groshong catheter); 3) cuffed central venous silicone catheters that are tunneled underneath the skin to reduce infection (e.g., Broviac, Leonard and Hickman catheters); 4) dual lumen catheters having a tapered tip and two adjacent holes communicating with one lumen just proximal to the tip to assist with outflow, and two adjacent holes communicating with the other lumen (180 degrees removed) just proximal to the first set of holes to assist with inflow (e.g., the Mahurkar catheter); 5) dual lumen catheters having a diverting structure consisting of a shoulder that has a straight up distal face and a sloped proximal face to reduce access recirculation and raise pressure in the vicinity of the inlet aperture (U.S. Pat. No. 6,409,700); and 6) catheters designed for femoral approach having two sets of staggered side ports, resulting in a total of four side ports.

One problem with existing multi-lumen catheters is that such catheters can experience decreased flow rates over time. Decreased flow rates may be caused by, among other things, blockage of the aspiration and/or infusion ports in the catheter. Various factors can cause a port to become blocked. One common cause of port blockage is the inadvertent positioning of one or more ports of the catheter against the vessel wall. This positioning hinders the free flow of fluid through the obstructed port, and in some cases, prevents fluid flow altogether. Another common cause of port blockage is the formation of fibrin sheaths along the ports. Fibrin sheaths may be formed, e.g., in response to the vessel wall washing effect or clotting.

Decreased, or restricted, flow is clearly undesirable in a multi-lumen for use in extracorporeal treatment of a fluid, such as a hemodialysis catheter. In order for the extracorporeal fluid treatment to be effective, fluid flow through the catheter must not be restricted in any appreciable way. Thus, it is important to position existing catheters in a manner such that fluid flow is not restricted. Additionally, it is important to insure that all ports are unobstructed.

Various attempts have been made in the art to reduce port blockage. For example, as described above, some catheters are provided with side ports at various locations on the catheter. Side ports generally provide some reduction in port blockage, however such ports themselves are subject to blockage when placed against the vessel wall, or as a result of fibrin formation on the port. Other attempts have been made to reduce port blockage by providing the staggered side-by-side dual lumen design described above, wherein the respective aspiration and infusion tubes are of different lengths so that the ports aspirate and infuse the bodily fluid at different axial locations of the catheter. While this arrangement may avoid some problems involved in maintaining adequate flow through the lumens, such catheters can still be subject to suboptimal flow. Some catheters, such as the Mahurkar catheter described above, must be rotated if inflow is blocked because the catheter is up against the vein wall. Although each of these techniques may be at least partially effective in reducing some types of blockage, reduced flow rate continues to be a problem in the art.

It is desired to provide a multi-lumen catheter assembly for use in the extracorporeal treatment of bodily fluids, wherein the multi-lumen catheter assembly is structured in a manner to minimize port blockage, and to provide for optimal fluid flow through the lumens of the catheter.

SUMMARY

The shortcomings of the prior art are addressed by the present invention. In one form thereof, the invention comprises a catheter assembly comprising a catheter body having a plurality of lumens extending therein. The catheter body has an aspiration port in communication with a first lumen for transporting fluid withdrawn from a body vessel, and an infusion port in communication with a second lumen for return of fluid to the vessel. The catheter body comprises a flap portion extending radially from the catheter body and defining the aspiration port. The flap portion is configured and arranged to space the aspiration port from a wall of the body vessel.

In another form thereof the invention comprises a catheter assembly for use in the extracorporeal treatment of a body fluid of a patient. The catheter assembly comprises an elongated catheter body having a proximal end, a distal end, a pair of lumens extending at least substantially therethrough, and a septum separating the lumens. One of the lumens comprises an aspiration lumen, and the other lumen comprises an infusion lumen. An aspiration port is disposed along a length of the catheter body in communication with the aspiration lumen for receiving body fluid from a body vessel of the patient for transport to a treatment unit, and an infusion port is disposed in communication with the infusion lumen for returning treated body fluid to the vessel. The catheter body includes a flap portion extending radially therefrom and defining the aspiration port. The flap portion is structured to substantially maintain the radial extension from the catheter body when inserted into the body vessel and engaging a wall of the vessel.

In yet another form thereof, the invention comprises a method for treating a body fluid. An assembly is provided for transporting the body fluid. The assembly comprises a catheter body having a plurality of lumens extending therein. The catheter body has an aspiration port in communication with a first lumen for transporting fluid withdrawn from a body vessel, and an infusion port in communication with a second lumen for returning fluid to the vessel. The catheter body comprises a flap extending radially from the catheter body and defining the aspiration port. The flap is structured to substantially maintain the radial extension from the catheter body when inserted into the body vessel and engaging a wall of the vessel. A distal end of the assembly is inserted into the vessel, and the body fluid to be treated is aspirated from the vessel through the aspiration port. The aspirated fluid is transported through the first lumen to a treatment instrument. The fluid is treated in the treatment instrument, and treated fluid is thereafter transported from the treatment instrument through the second lumen. The treated fluid is then infused back into the body vessel through the infusion port.

BRIEF DESCRIPTION OF THE DRAWINGS

FIG. 2 is an enlarged side view of the distal portion of the catheter assembly of FIG. 1;

FIG. 3 is a longitudinal sectional view of the catheter assembly taken along line 3-3 of FIG. 2;

FIG. 4 is a transverse sectional view of the catheter assembly, taken along line 4-4 of FIG. 2;

FIG. 5 is a side view of the distal portion of the catheter assembly rotated 90 degrees in a first direction from the view of FIG. 2;

FIG. 6 is an end view of the catheter assembly shown in FIG. 5;

FIG. 7 is a side view of the distal portion of the catheter assembly rotated 90 degrees in a second direction from the view of FIG. 2;

FIG. 8 is an enlarged side view of the catheter assembly of FIG. 2, wherein an introducer is provided over the distal end of the catheter body.

DETAILED DESCRIPTION OF THE DRAWINGS AND THE PRESENTLY PREFERRED EMBODIMENTS

Figure 1:
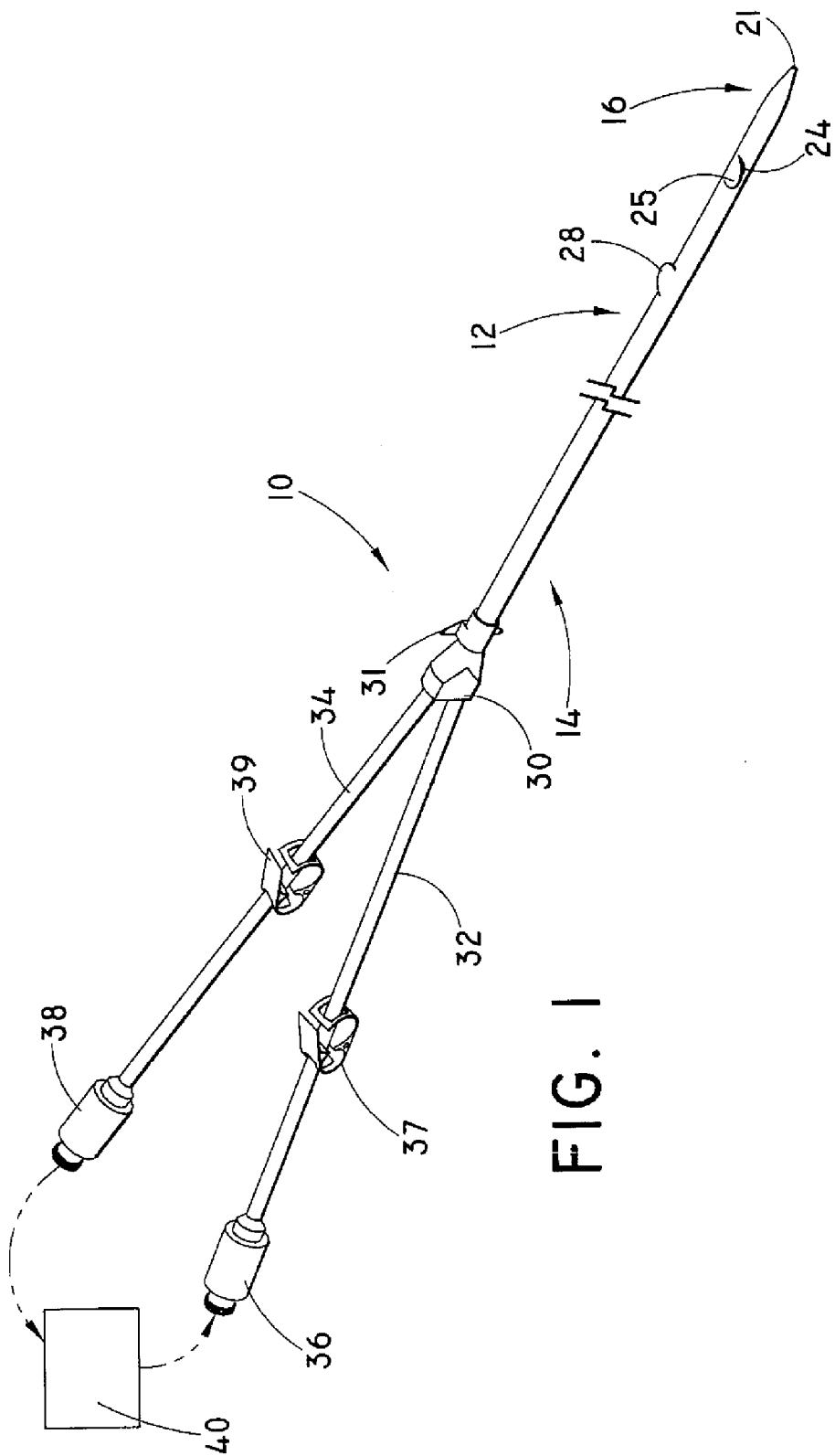
FIG. 1 is a perspective view of a catheter assembly according to one embodiment of the present invention.

For purposes of promoting an understanding of the present invention, reference will now be made to the embodiments illustrated in the drawings, and specific language will be used to describe the same. It is nevertheless to be understood that no limitation of the scope of the invention is thereby intended, the scope of the invention being indicated by the claims appended below and the equivalents thereof. The figures are not all drawn to the same scale to avoid obscuring the details of the finer structures. The following detailed description of the preferred embodiments will make clear the preferred arrangement, size relationships and manner of using the components shown herein.

The present invention is directed to a catheter assembly for use in the extracorporeal treatment of bodily fluids. The bodily fluids are transported from the body through an aspiration lumen in the catheter, and are thereafter transported to an instrument for extracorporeal treatment. The treated fluids are then returned to the body through an infusion lumen in the catheter. Those skilled in the art will appreciate that the inventive extracorporeal catheter is suitable for multiple uses involving inflow and outflow of bodily fluids. For convenience, the invention will be primarily described hereinafter with reference to one of its intended uses, namely as a hemodialysis catheter for use in the extracorporeal treatment of blood. The hemodialysis catheter enables blood inflow without disruption, and blood return without hemolysis. In addition to hemodialysis, the catheter can be used for other extracorporeal fluid treatments in which a body fluid is withdrawn from the body, subjected to a treatment process, and thereafter returned to the body. Pheresis and hemofiltration are non-limiting examples of such procedures.

In the following discussion, the terms "proximal" and "distal" will be used to describe the axial ends of the catheter assembly, as well as the axial ends of various component features. The "proximal" end refers to the end of the catheter assembly (or component) that is closest to the operator during use of the assembly. The "distal" end refers to the end of the assembly (or component) that is initially inserted into the patient, or that is closest to the patient during use.

FIG. 1 is a perspective view of a catheter assembly 10 according to one embodiment of the present invention. Catheter assembly 10 includes a catheter body 12. Catheter body 12 comprises an elongated tubular member formed of a conventional polymer commonly used for such purposes in medical catheters, such as radiopaque polyurethane. Other conventional materials used for such purposes in the medical device art may be substituted. Non-limiting examples of such materials include silicone, polyurethane and PTFE. Catheter body 12 has a proximal end 14, a tapered distal end 16, and includes lumens 18, 20 extending at least partially therethrough (FIGS. 3, 4).

In the preferred embodiment shown, catheter assembly 10 includes a bifurcated fitting, such as manifold 30. Manifold 30 may be provided with conventional suture wings 31 if desired. Extension tubes 32, 34 extend in the proximal direction from manifold 30. Extension tubes 32, 34 comprise generally flexible polymers commonly used for such purposes in the medical device art, such as polyurethane, PVC and silicone. Catheter body 12 is received in manifold 30 in conventional fashion, such as by insert molding catheter body proximal end 14 in a suitably-sized channel in manifold 30. Extension tube 32 communicates with fluid aspiration lumen 18 in catheter body 12 for receiving fluid withdrawn from a body vessel in the patient. A luer lock or other suitable connector 36 is fitted onto the proximal end of extension tube 32 in conventional fashion.

During use of catheter assembly 10, connector 36 is engaged in mating relationship with a connector associated with an ingress opening of a treatment instrument 40, such as a dialyzer, for establishing a flow path of blood to the dialyzer. Extension tube 34 communicates with blood infusion lumen 20 in catheter body 12. A luer lock or other suitable connector 38 is fitted onto the proximal end of extension tube 34. Connector 38 is engaged in mating relationship with a connector associated with an egress opening of dialyzer 40 for receiving treated blood from the dialyzer. Dialyzer 40 and its ingress and egress openings are shown schematically in FIG. 1. Conventional clamps 37, 39 may be provided for selectively controlling the flow of blood between the dialyzer and the catheter body.

FIG. 2 is an enlarged side view of the distal portion of the catheter assembly 10 of FIG. 1. FIG. 3 is a longitudinal sectional view of catheter assembly 10 taken along line 3-3 of FIG. 2. FIG. 4 is a transverse sectional view of catheter assembly 10, taken along line 4-4 of FIG. 2. FIGS. 3 and 4 illustrate the lumens 18, 20, that extend longitudinally through at least the major portion of the length of catheter body 12. In the preferred arrangement depicted in the figures, lumen 18 is the fluid aspiration, or withdrawal, lumen, and lumen 20 is the fluid infusion, or return, lumen. Those skilled in the art will appreciate that with minor modification, this arrangement of lumens can be reversed. Septum 22 is provided internally of catheter body 12 to separate lumens 18 and 20. In the embodiment shown, aspiration lumen 18 extends from aspiration port 24 to the proximal end of catheter body 12.

FIG. 5 is a side view of the distal portion of the catheter assembly rotated 90 degrees in a first direction from the view of FIG. 2. FIG. 6 is an end view of the catheter assembly shown in FIG. 5. FIG. 7 is a side view of the distal portion of the catheter assembly rotated 90 degrees in a second direction from the view of FIG. 2.

In the embodiment shown in the figures, a flap 25 is molded or otherwise formed in catheter body 12. Flap 25 extends outwardly from catheter body 12 in the nature of a "wing." Aspiration port 24 is defined by the distension of flap 25 from main catheter body 12. In a preferred embodiment, a second wing-like flap 28 is molded or otherwise formed in catheter body 12 proximal to flap 25 to define a second aspiration port 27. Each aspiration port communicates with aspiration lumen 18, thereby providing a passageway for fluid to aspirate from the vessel into the lumen. Preferably, beading 29 or other "filler" material is provided in the space between aspiration port 24 and the closed distal end 19 of lumen 18, as shown in FIG. 3. Adding filler material to the otherwise unused, or "dead", space distal of the aspiration port increases the efficiency of the flow. If desired, additional aspiration ports can be formed along the length of catheter body 12 to increase fluid flow into the aspiration lumen 18. When present, such additional ports are also preferably defined by flaps as described above, however this is not necessarily required, and such additional ports may have other configurations suitable for aspiration of a fluid.

Fluid infusion lumen 20 typically extends from infusion port 21 to the proximal end of catheter body 12. In the preferred embodiment shown, infusion port 21 comprises an opening at the distal end of catheter body 12 in communication with infusion lumen 20. If desired, one or more side ports 23 may be provided along the length of catheter body 12 that also communicate with infusion lumen 20. Side port 23 provides extra surface area for infusion of treated blood into the vessel in addition to infusion port 21. Preferably, aspiration ports 24 and 27 are positioned proximal to infusion port 21 and side port 23 along the length of catheter body 12. This arrangement is preferred, but not crucial to the invention. Positioning the aspiration port(s) proximal to the infusion port and side port(s) enhances the efficiency of the extracorporeal procedure, by assuring that the majority of the blood that is aspirated through the aspiration port(s) is not the same blood that has previously been cleansed and returned to the vessel through the infusion port and/or side port.

Flaps 25, 28 are configured and positioned such that catheter body 12 resists direct apposition with the vessel wall. The "wing-like" extension of flaps 25, 28 from catheter body 12 increases the effective radial diameter of the catheter at the site of the wings, thereby distending the vessel wall away from intimate contact with the underlying aspiration port openings 24, 27. Preferably, flaps 25, 28 are formed and configured such that they are capable of assuming a low profile upon insertion or removal, and thereafter flaring radially once positioned at the treatment site in the vessel.

In a preferred embodiment, an introducer sheath 50 (FIG. 8) may be provided over the distal end of catheter assembly 10. In FIG. 8, introducer sheath 50 is shown partially extended in the proximal direction. In this position, introducer sheath 50 covers a portion of flap 25, thereby urging flap 25 into close association with catheter body 12. When sheath 50 is fully extended in the proximal direction it covers each of flaps 25, 28. As a result, flaps 25, 28 assume a low radial profile, such that the radial distension of each flap is substantially reduced, or eliminated altogether. Flaps 25, 28 remain in this low profile condition as long as sheath 50 is in place on the catheter body.

In the non-limiting embodiment shown, sheath 50 comprises a splittable structure having an elongated body 52 that tapers to a distal end 54 dimensioned for insertion into the body vessel. Elongated body 52 is dimensioned to receive the distal end of catheter body 12 therein in a snugly-fitting relationship. A pair of ears 55, 56 is provided, which ears may include graspable knobs 57, 58 for use in splitting the elongated body 52. Splittable introducer sheaths are well known in the medical arts, and a skilled artisan is well aware of the manner of use and splitting of such sheaths. Splittable introducer sheaths are commercially available, e.g., from Cook Incorporated, of Bloomington, Ind., as PEEL-AWAY® introducers.

During one mode of use of catheter assembly 10, the leading (distal) end 54 of sheath 50 is initially inserted into an opening in the vessel. Preferably, the catheter assembly and introducer sheath are introduced over a wire guide that has previously been positioned in the vessel by conventional means, such as the well-known Seldinger technique. Following insertion of the catheter assembly and sheath, the wire guide is removed. The sheath is thereafter removed by grasping and pulling the knobs in an outward direction and peeling the sides of the sheath in well-known fashion, leaving the leading (distal) end of the catheter assembly in position in the vessel.

Although it is preferred to introduce the catheter assembly with the use of an introducer sheath, such as splittable sheath 50, this is not required. The use of an introducer sheath is not always necessary, and in some occasions the catheter assembly can be successfully introduced without the use of such a sheath or other introducing device. Those skilled in the art will appreciate that a generally radial force is applied to the flaps upon insertion into the vessel by the adjacent tissue at the insertion site. This force will cause the flaps to collapse upon insertion, in the same manner as the force of an introducer sheath covering the flaps. Upon entering the vessel, the force is removed, and the flaps expand to the wing-like configuration shown and described. The same principle applies during removal of the catheter assembly from the vessel.

As stated, flaps 25, 28 are preferably formed from catheter body 12. In a preferred embodiment, a crescent-shaped cut is formed in the catheter body wall to define the flaps. Those skilled in the art will appreciate, however, that cuts formed in other routine geometric shapes, such as a portion of an ellipse, polygon, parabola, etc., are also suitable. The cuts, such as the crescent-shaped cut described above, may be formed in catheter body 12 in any convenient manner, such as by the use of a small hole-saw. Those skilled in the art can readily determine other suitable means for forming the initial cut in the catheter body. Preferably, the length of the cut (in the axial direction) will be roughly two times the diameter of the catheter, although other dimensions may be substituted if desired.

Once the flaps in the catheter body are cut to the desired size and shape, the flaps are preferably set in a manner to maintain the distended wing-like configuration relative to the remainder of the catheter body. One preferred manner of setting the flaps is by a conventional heat-set or steam-set procedure. Other conventional physical and chemical setting procedures may alternatively be used. The particular mode of setting the flap is generally not important, as long as the resulting flap has sufficient strength and structural integrity to at least substantially maintain its distended, or wing-like, configuration under conditions expected to be encountered in the body vessel. When optimally formed and set, the flaps are oriented and configured to be substantially atraumatic to tissue, and to be substantially snag resistant when positioned in the vessel.

Those skilled in the art will appreciate that the cutting and setting technique described above is not the only way to form a suitable flap in a catheter body, and that this structure may also be arrived at by alternative means. One such alternative involves injection molding a multi-lumen catheter to include one or more flaps, and corresponding ports, of suitable size and shape to communicate with a selected lumen.

Figure 9:
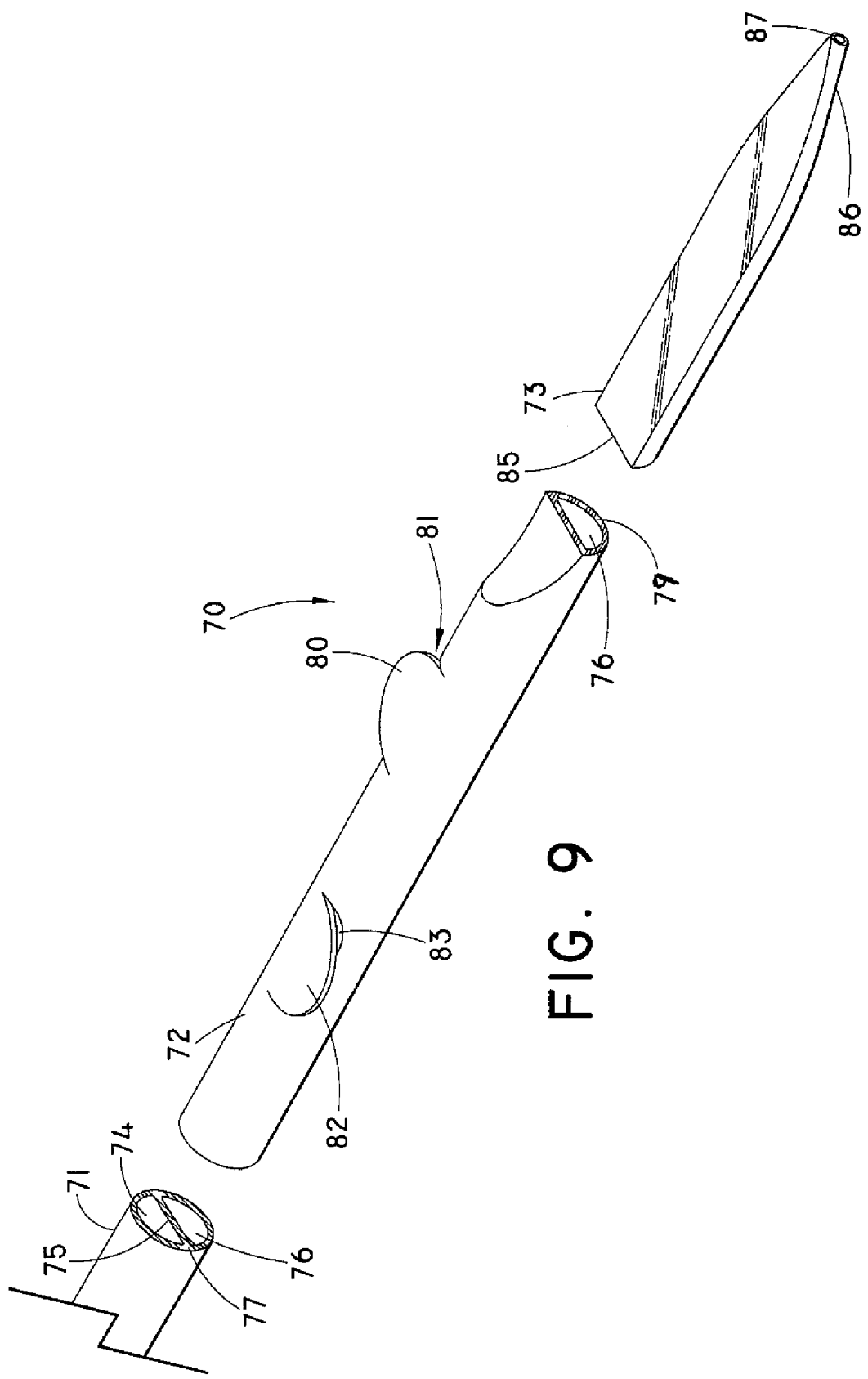
FIG. 9 is an exploded view of another embodiment of a catheter assembly.

As a variation of the molding operation described above, the catheter body can be formed from multiple initially separate components, which components are alignable for assembly into a unitary elongated body. FIG. 9 illustrates an exploded view of a catheter assembly 70 formed of three catheter body segments 71, 72, 73. Although this preferred embodiment includes three initially separate components, more, or fewer, such components may be utilized in a particular case.

Catheter body segment 71 is generally similar to catheter body 12 of the previous embodiments, and comprises a major length of the catheter body. In the embodiment shown, lumen 74 is the aspiration (withdrawal) lumen, and lumen 76 is the infusion (return) lumen. A septum 75 separates lumens 74, 76. Catheter body segment 71 terminates at a blunt distal end 77. Lumens 74, 76 extend at least substantially through the unitary body.

In this embodiment, catheter body segment 72 is molded, such as via a conventional injection molding process, to the general shape illustrated in the figure. Segment 72 includes one or more flaps, such as flaps 80, 82. Flaps 80, 82 define aspiration ports 81, 83, which ports are in communication with aspiration lumen 74. Aspiration lumen 74 terminates in the distal direction within body segment 72, and a filler material, similar to filler material 29 described above and illustrated schematically in FIG. 3, may extend within the dead space of the lumen to the distal end of the body segment. Preferably, the distal end 79 of body segment 72 includes a smooth tapered contour as shown.

Catheter body segment 73 is configured such that proximal end 85 matches the contour of distal end 79 of body segment 72. Distal end 86 tapers to open tip portion 87 to facilitate insertion into the vessel. Open tip portion 87 communicates with infusion lumen 76, and defines an infusion port for return of treated fluid to the vessel. One or more side ports (not shown) may be provided if desired. Devices for forming tip configurations are well known in the medical arts, and those skilled in the art can readily adapt such a device to form body segment 73.

When a catheter is formed from one or more body segments as shown in the embodiment of FIG. 9, all, or some, of the segments may be molded. Molding may be particularly appropriate for the segment (72) that includes the flap(s) and the aspiration port(s), as it provides a very convenient way of forming the requisite structure (flaps and ports). The molded segment may then be attached by conventional means, such as adhesion, bonding, etc., to adjoining body segments, such as segments 71 and 73, which segments 71, 73 may, or may not, be molded. In order to provide a secure attachment between the segments, it is preferred that the respective segments be formed from the same, or a similar, composition.

The methods of forming the catheter body and flaps described herein are intended to be exemplary, and not exclusive. When armed with the teachings of the present invention, those skilled in the art are readily capable of forming a suitable catheter as described herein, wherein the catheter body includes a flap that defines an underlying port, and which flap has sufficient strength and structural integrity to at least substantially maintain its distended configuration under conditions typically encountered in a body vessel.

The features described above can be supplemented with other known materials and techniques to improve various properties of the catheter assembly. For example, one or more radiopaque markers can be added along the length of the catheter body, or a radiopaque material may be added to the matrix of all or a part of the catheter body to improve visualization of the catheter in accordance with well-known techniques. Similarly, the catheter body may include a hydrophilic coating along all or a part of the length of the catheter to facilitate entry into the vessel. As yet another alternative, the catheter body can be coated with various medicaments along all or a part of the length of the catheter body. Non-limiting examples of such medicaments include antiproliferatives, anticoagulants, thrombolytics, fibrinolytics, and anti-microbials.

Although the figures provided herein illustrate single body catheters such as the COOK DDS catheters, available from Cook Critical Care, of Bloomington, Ind., those skilled in the art will recognize that the invention is equally applicable with only minor modification to use with other conventional catheters, such as split-body catheters.

It is therefore intended that the foregoing detailed description be regarded as illustrative rather than limiting, and that it be understood that it is the following claims, including all equivalents, that are intended to define the spirit and scope of this invention.

The invention claimed is:

1. A catheter assembly, comprising:
   a catheter body having a plurality of lumens extending therein, said catheter body having an aspiration port in communication with a first lumen for transporting fluid withdrawn from a body vessel, said first lumen having a closed distal end, and an infusion port in communication with a second lumen for return of fluid to said vessel, said infusion port positioned distal of the aspiration port along a length of the catheter body; said catheter body comprising a flap portion extending radially from said catheter body and defining said aspiration port, said flap portion configured and arranged to space said aspiration port from a wall of said body vessel.

2. The catheter assembly of claim 1, wherein said catheter body includes a septum separating said first and second lumens, said septum extending at least substantially to said infusion port along said catheter body length.

3. The catheter assembly of claim 1, wherein said flap portion comprises a geometrically-shaped member formed from said catheter body, said flap portion being structured to substantially maintain said radial extension from said catheter body when inserted into said body vessel and engaging said vessel wall.

4. The catheter assembly of claim 3, wherein said flap portion is heat set to maintain said radial extension.

5. The catheter assembly of claim 3, wherein said aspiration port comprises a first aspiration port, said catheter body further comprising a second aspiration port disposed along said catheter body length, said second aspiration port in communication with said first lumen.

6. The catheter assembly of claim 5, wherein said catheter body comprises a second flap portion extending radially from said catheter body, said second flap portion defining said second aspiration port, said second flap portion comprising a geometrically-shaped member and being structured to substantially maintain said radial extension from said catheter body when inserted into said body vessel and engaging said vessel wall, said second aspiration port being disposed proximal of said first aspiration port.

7. The catheter assembly of claim 3, wherein said catheter body further includes at least one side port communicating with said infusion lumen.

8. The catheter assembly of claim 1, further comprising a removable sheath member sized to be received over a distal end portion of said catheter body for reducing the radial extension of said flap portion.

9. The catheter assembly of claim 8, wherein said sheath member comprises a longitudinally splittable sheath body.

10. The catheter assembly of claim 1, wherein said catheter body comprises a plurality of longitudinally aligned body segments, a first one of said segments comprising a major length of said catheter body, and said flap portion and said aspiration port disposed along a second one of said segments.

11. The catheter assembly of claim 10, wherein at least the second segment is molded.

12. The catheter assembly of claim 1, wherein a filler material is disposed along said first lumen between said aspiration port and said closed distal end.

13. A catheter assembly for use in the extracorporeal treatment of a body fluid of a patient, comprising:

an elongated catheter body having a proximal end, a distal end, a pair of lumens extending at least substantially therethrough, and a septum separating said lumens, one of said lumens comprising an aspiration lumen, and the other of said lumens comprising an infusion lumen, said aspiration lumen extending to a closed distal end along a length of said catheter body, an aspiration port disposed along a side of said catheter body proximal of said closed distal end, said aspiration port in communication with said aspiration lumen for receiving body fluid from a body vessel of said patient for transport to a treatment unit, and an infusion port in communication with said infusion lumen for returning treated body fluid to said vessel, said catheter body comprising a flap portion extending transversely therefrom at said aspiration port, said flap portion being formed from said catheter body, and structured to substantially maintain said transverse extension from said catheter body when inserted into said body vessel and engaging a wall of said vessel, said aspiration port disposed proximal to said infusion port along said catheter body length, said septum extending at least substantially to said infusion port along said catheter body length.

14. The catheter assembly of claim 13, wherein said catheter body distal end tapers to an open distal tip, and wherein said open distal tip comprises said infusion port.

15. The catheter assembly of claim 14, wherein said aspiration port comprises a first aspiration port, said catheter body further comprising a second aspiration port disposed along a side of said catheter body proximal of said first aspiration port, said catheter body comprising a second flap portion extending transversely from said catheter body, said second flap portion defining said second aspiration port and being structured to substantially maintain said transverse extension from said catheter body when inserted into said body vessel and engaging a wall of said vessel.

* * * * *